United States Patent
Bell

[11] Patent Number: 5,935,051
[45] Date of Patent: Aug. 10, 1999

[54] BLOOD SEPARATION DEVICE

[75] Inventor: Michael L. Bell, Fullerton, Calif.

[73] Assignee: Beckman Instruments, Inc., Fullerton, Calif.

[21] Appl. No.: 08/920,746

[22] Filed: Aug. 29, 1997

[51] Int. Cl.$^6$ .............................. B04B 1/16; B04B 1/10; B04B 9/10

[52] U.S. Cl. .................. 494/4; 210/85; 210/86; 494/7; 494/10; 494/40; 494/56

[58] Field of Search ............. 210/85, 86, 360.1, 210/361, 117, 390; 422/72; 494/1, 2, 4, 7, 10, 19, 40, 56, 60

[56] References Cited

U.S. PATENT DOCUMENTS

| | | | |
|---|---|---|---|
| 1,751,982 | 3/1930 | Dunham | 494/4 |
| 2,542,456 | 2/1951 | Ayres | 494/2 |
| 2,635,617 | 4/1953 | Condell | 494/4 |
| 2,654,536 | 10/1953 | Heckendorf | 494/4 |
| 3,244,363 | 4/1966 | Hein | 494/40 |
| 3,261,546 | 7/1966 | Gruver, Jr. | 494/3 |
| 3,369,742 | 2/1968 | Weiland | 494/4 |
| 3,684,450 | 8/1972 | Adler et al. | 494/2 |
| 3,752,389 | 8/1973 | Nilsson | 494/3 |
| 3,918,920 | 11/1975 | Barber | 422/104 |
| 3,986,663 | 10/1976 | Jonsson et al. | 494/3 |
| 4,197,287 | 4/1980 | Piasio et al. | 424/1 |
| 4,325,825 | 4/1982 | Schutte | 494/3 |
| 4,762,798 | 8/1988 | Deutsch | 436/67 |
| 4,820,256 | 4/1989 | Nordstrom | 494/40 |
| 4,846,974 | 7/1989 | Kelley et al. | 210/380.1 |
| 4,865,813 | 9/1989 | Leon | 422/101 |
| 4,981,585 | 1/1991 | Kelley et al. | 210/138 |
| 5,308,506 | 5/1994 | McEwen et al. | 210/745 |
| 5,455,009 | 10/1995 | Vogler et al. | 422/102 |

*Primary Examiner*—John Kim
*Attorney, Agent, or Firm*—William H. May; P. R. Harder; Steven G. Roeder

[57] ABSTRACT

A separator and a method for quickly separating an aliquot of plasma or serum from cells in a sample of blood is provided herein. The separator includes a housing which defines a separation container, an outlet aperture, a valve which selectively seals the outlet aperture, and a spinner. Initially, the spinner rotates the housing at a separation speed which causes the heavier cells to separate from the serum or plasma. Subsequently, the spinner rotates the housing at a faster, expellant speed which causes the valve to open and the cells to be expelled through the outlet aperture. After the cells have been expelled from the separation container, rotation of the housing is stopped and the serum or plasma is collected from the separation container. Since the separator provided herein does not use a separation gel, the separator is easy to clean and reusable.

24 Claims, 3 Drawing Sheets

BLOOD SEPARATION DEVICE

FIELD OF THE INVENTION

The present invention pertains generally to a device and method for separating a sample of whole blood. More specifically, the present invention relates to a reusable separator and method for quickly separating an aliquot of plasma or serum from a sample of whole blood.

BACKGROUND OF THE INVENTION

Samples of blood are frequently taken from a patient to evaluate the health of a patient and/or to evaluate what measures are necessary to restore the health of a patient. In most cases, a clinical analyzer is used to analyze the sample of blood. The clinical analyzer is commonly able to perform a number of tests, such as drug discovery, specific protein blood analysis, and/or cancer detection from the sample of blood.

Typically, the analysis on the sample of blood is performed only on a liquid portion of the blood sample. The liquid portion of the blood sample is plasma, if the sample has been treated with anticoagulants. Alternately, if the sample has not been treated with anticoagulants, the liquid portion is serum. Therefore, it is often necessary to separate the plasma or serum from cells of the sample of blood prior to analysis with the clinical analyzer.

Currently, separation of the serum or plasma from the sample of blood is achieved by centrifuging a separation tube containing the sample of blood and a separation gel. Unfortunately, the time required to separate the plasma or serum from the sample using a common centrifuge varies between about five (5) and fifteen (15) minutes. Further, the common centrifuge requires a significant amount of lab space. Accordingly, a significant amount of lab time and lab space is needed to separate the serum or plasma from the cells.

In order to save lab time and lab space, a number of samples are commonly processed simultaneously, i.e., "batch processed," at a remote location. However, this can lead to delays and wasted clinical analyzer time waiting for multiple samples to be batch processed at the remote location.

Moreover, since a separation gel is utilized, the separation tube is difficult to clean and new separation gel is difficult to re-supply to the separation tube. Thus, the used separation tube and the used separation gel typically become medical waste.

In light of the above, it is an object of the present invention to provide a device and method which quickly separates an aliquot of plasma or serum from a sample of blood. Another object of the present invention is to provide a device and method which is relatively easy to use and does not utilize a significant amount of laboratory space. Yet another object of the present invention is to provide a device and method for separating an aliquot of plasma or serum from a sample of blood which is relatively easy to clean and is reusable. Still another object of the present invention is to provide a device which can be incorporated as an integral part of a clinical analyzer, so that the sample of whole blood can be presented directly to the clinical analyzer.

SUMMARY

The present invention is directed to a separator and a method for separating a blood sample which meets these objectives. The separator includes a housing defining a separation container, an outlet aperture, and a valve. As provided in detail below, the housing is initially rotated at a separation speed to separate the blood sample within the separation container. Subsequently, the housing is rotated at an expellant speed to open the valve and expel cells from the sample from the separation container. Thus, the separator relies upon centrifugal force to separate the sample, open the valve, and expel the cells. Therefore, separation of the sample can be accomplished by simply controlling the rotation speed of the housing.

As used herein, the term "first portion" means and refers to the portion of the sample which is expelled from the separation container. For a sample having elements with different densities, the first portion is the heavier elements of the sample. For example, in a sample of blood, the first portion is the cells. Alternately, if all of the elements of the sample have substantially the same density, the first portion is the portion which is closest to the outlet aperture which is expelled.

As used herein, the term "second portion" means and refers to the portion of the sample which remains in the separation container after completion of the process provided herein. Typically, for a sample having elements of different densities, the second portion is the lighter elements of the sample. For example, in a sample of blood, the second portion is the plasma or serum from the blood, depending upon whether the sample of blood has been treated with an anticoagulant. Alternately, if all of the elements of the sample have substantially the same density, the second portion is the portion of the sample which is farthest from the outlet aperture, which remains in the separation container.

As used herein, the term "test specimen" means and refers to either plasma or serum.

The separation container includes a distal region, a proximal region, and an outlet region. The outlet region is positioned between the distal region and the proximal region. Preferably, the separation container is substantially symmetrical about a container axis and has a container cross-section, perpendicular to the container axis, which is widest proximate the outlet region. With this configuration, the heavier cells will migrate towards the outlet region during rotation of the housing.

The valve substantially seals the outlet aperture during non-rotation of the housing and rotation at or below the separation speed. Importantly, the valve opens when the housing is rotated at or above the expellant speed to expel the cells from the separation container.

As provided herein, the valve can be a tubular "O" ring type seal which encircles the housing and covers the outlet opening. As described in detail below, the centrifugal force acting on the "O" ring seal during rotation at or above the expellant speed overcomes the elastic restoring force of the "O" ring. This results in the expansion of the "O" ring and the unsealing of the outlet aperture.

The separator can include a retainer for retaining the valve in position on the housing. For a valve which includes an "O" ring type seal, the retainer can include a groove extending substantially circumferentially around an outer surface of the separation housing, proximate the outlet region.

A spinner can be used for selectively rotating the separation housing. More particularly, for a sample of blood, the spinner initially rotates the separation container at the separation speed to separate the cells from the test component within the separation container. Subsequently, the spinner rotates the separation container at the expellant speed to open the valve and expel the cells through the outlet aperture.

The present invention is also a method for separating a test specimen from cells in a sample of blood. The method includes introducing the sample of blood into a separation container, spinning the separation container, and expelling the cells through an outlet aperture in the separation container while the separation container is spinning. Preferably, the separation container is spun about the container axis to reduce the time necessary to separate the sample.

Importantly, the separator quickly separates an aliquot of plasma or serum from a sample of whole blood. Further, the separator does not require a lot of lab space and is easily reusable. Thus, the separator can be used as an integral part of a clinical analyzer. This eliminates an external sample preparation step and allows the sample of whole blood to be supplied directly to the clinical analyzer.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
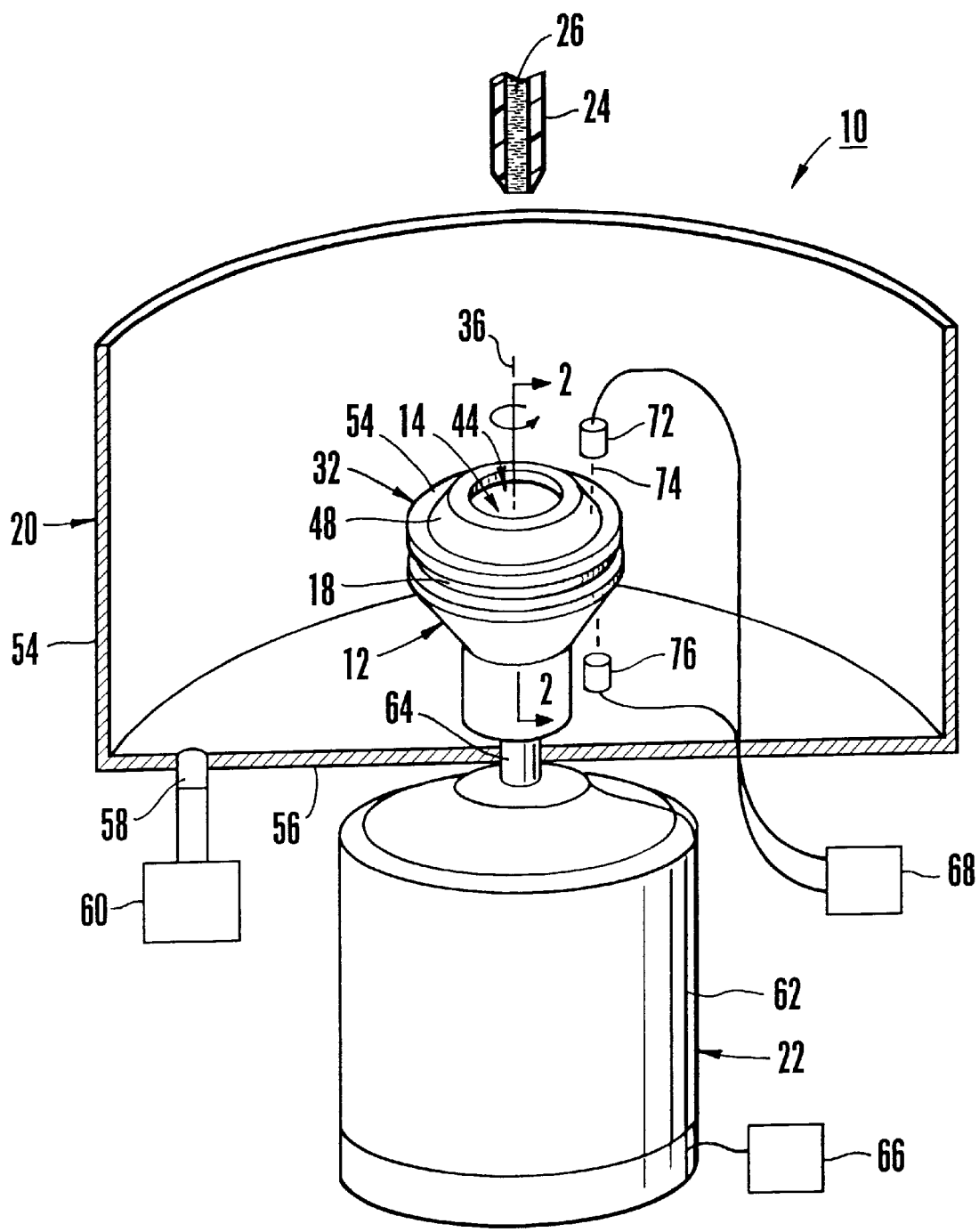
FIG. 1 is a perspective view of a separator having features of the present invention, an outer receptacle and a probe are shown in cutaway for clarity.

Referring initially to FIG. 1, a separator 10 according to the present invention includes a housing 12 having a separation container 14 and an outlet aperture 16 (not shown in FIG. 1), a valve 18, an outer receptacle 20, and a spinner 22. FIG. 1 also shows a probe 24 which moves a sample 26 to and from the separator 10.

As provided below, the separator 10 quickly separates an aliquot of serum or plasma from cells in a sample 26 of blood. This is accomplished by initially rotating the housing 12 with the spinner 22 at a separation speed to separate the sample 26 in the separation container 14. Subsequently, the housing 12 is rotated at an expellant speed to expel the cells from the separation container 14 through the outlet aperture 16. Since the present invention does not require the use of a separation gel (not shown) to separate the sample 26 of blood, the separator 10 is relatively easy to clean and is reusable. Further, the separator 10 is relatively simple to use since the separator 10 only requires a single axis of rotation and controllable speed.

Although the present invention is particularly useful for separating a sample 26 of blood, the separator 10 provided herein may be used for separating, mixing and/or selectively removing a portion of other biological or chemical samples. For example, the present invention may be useful for mixing and separating samples 26 for biological or chemical assays or the sample 26 could be a reaction mixture used for heterogeneous immunoassays.

As previously provided, the term "first portion" 28 (shown in FIGS. 4 and 5) means and refers to the portion of the sample 26 which is expelled from the separation container 14. For a sample 26 having elements with different densities, the first portion 28 is the heavier elements of the sample 26. For example, for a sample 26 of blood, the first portion 28 is the cells. Alternately, if all of the elements of the sample 26 have substantially the same density, the first portion 28 is the portion which is closest to the outlet aperture 16 which is expelled.

Also as previously provided, the term "second portion" 30 (shown in FIGS. 4 and 7) means and refers to the portion of the sample 26 which remains in the separation container 14 after completion of the process provided herein. Typically, for a sample 26 having elements with different densities, the second portion 30 is the lighter elements of the sample 26. For example, for a sample 26 of blood, the second portion 30 is the plasma or serum from the blood, depending upon whether the sample 26 of blood has been treated with an anticoagulant. Alternately, if all of the elements of the sample 26 have substantially the same density, the second portion 30 is the portion of the sample 26 which is farthest from the outlet aperture 16, which remains in the separation container 14.

Plasma and serum are also collectively referred to herein as the "test specimen."

The housing 12 includes the separation container 14 and a valve retainer 32. In the embodiment shown in the FIGS. 2–7, the housing 12 is shaped similar to a top and the separation container 14 is also shaped similar to a top. However, the shape of the housing 12 and the separation container 14 is not limited to the embodiments provided herein.

The separation container 14 shown in FIGS. 2–7 is substantially symmetrical about a container axis 36. The separation container 14 includes a distal region 38, a proximal region 40 and an outlet region 42. The outlet region 42 is positioned between the distal region 38 and the proximal region 40 and substantially encompasses the container axis 36.

In this embodiment, the separation container 14 has a cross-section, perpendicular to the container axis 36 and a diameter which varies between the proximal region 40 and the distal region 38. Preferably, the cross-section and diameter of the separation container 14 are the widest proximate the outlet region 42 and taper towards the distal region 38 and the proximal region 40. Stated another way, the housing 12 includes a cylindrical housing wall 43 which tapers from the outlet region 42 towards the distal region 38 and the proximal region 40. As can best be seen in FIGS. 3–6, this shape causes the sample 26 to migrate towards the outlet region 42 during rotation of the housing 12 about the container axis 36.

The required size of the separation container 14 varies according to the amount of sample 26 required to be separated. Presently, about 200–400 microliters of serum or plasma is required for analysis. Therefore, the separation container 14 provided herein retains about 500–700 microliters of sample 26.

The housing 12 also includes a container inlet 44 which allows ingress and egress into the separation container 14. Basically, the container inlet 44 allows the sample 26 to be placed into the separation container 14. Further, the container inlet 44 allows the second portion 30 to be removed from the separation container 14 after separation is complete. Alternately, the housing 12 can be spun until the second portion 30 is also expelled from the separation container 14.

Figure 3:
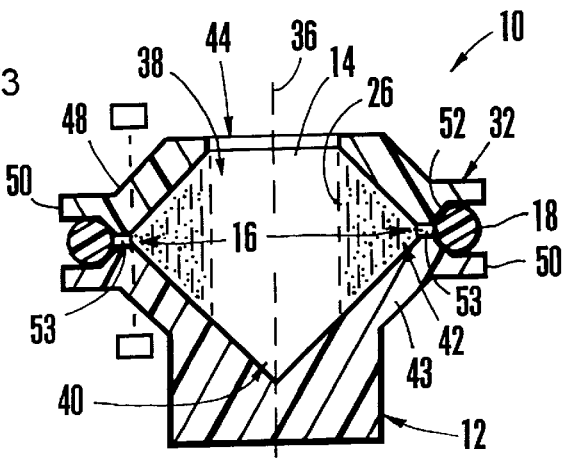
FIG. 3 is a cutaway view of the housing and the monitor of FIG. 2, after rotation of the housing begins.

In the embodiment shown in the Figures, the container inlet 44 is an opening proximate the distal region 38 of the separation container 14 which allows access into the separation container 14. Importantly, as can be seen in FIG. 3, the unique tapered shape of the separation container 14 inhibits the sample 26 from being forced out the container inlet 44 during operation of the separator 10. Alternately, the container inlet 44 could be located elsewhere and the separation container 14 could include an inlet cover (not shown) for selectively sealing the container inlet 44.

The valve retainer 32 retains the valve 18 to the housing 12. Typically, the valve retainer 32 is positioned proximate the outlet region 42 and holds the valve 18 proximate the outlet region 42. The design of the valve retainer 32 depends upon the design of the valve 18. In the embodiment shown in the Figures, the valve 18 is an "0" ring type seal. In this embodiment, the valve retainer 32 is a groove extending substantially circumferentially around an outer surface 48 of the housing 12. The groove includes a pair of outwardly extending circumferential walls 50 which are separated by a bottom surface 52 of the groove. Importantly, the walls 50 allow the "O" ring type seal to expand during rotation of the housing 12. The bottom surface 52 can be flat or beveled to facilitate engagement with the valve 18.

The first portion 28 is expelled through the outlet aperture 16 during rotation of the housing 12 at the expellant speed. The outlet aperture 16 is preferably positioned at the farthest point radially from the container axis 36, because the first portion 28 migrates there upon rotation of the housing 12. In the embodiment shown in FIGS. 2–7, the outlet aperture 16 extends between the outlet region 42 and the bottom surface 52 of the groove and is positioned radially away from the container axis 36.

As shown in FIGS. 2–7, the outlet aperture 16 can be a plurality of spaced apart holes 53 positioned circumferentially around the housing 12. In this embodiment, the holes 53 extend between the separation container 14 and the bottom surface 52 of the groove. If the outlet aperture 16 includes a plurality of holes 53, the housing 12 can be manufactured as an integral unit. Alternately, the outlet aperture 16 could be elongated openings (not shown) around the circumference of the housing 12 with intervening posts or material to retain the upper and lower portions of the housing together.

Optimumly, the housing 12 is manufactured from a substantially, transparent material so that the sample 26 can be monitored as provided below. Suitable materials for the housing 12 include acrylic, styrene, or a polycarbonate. Alternately, some or all of the housing 12 can be made from an opaque material.

The valve 18 substantially seals the outlet aperture 16 during non-rotation of the housing 12 and during rotation at or below the separation speed. Importantly, the valve 18 opens during rotation of the housing 12 at the expellant speed and allows the first portion 28 to be expelled from the separation container 14. The valve 18 can be implemented in a number of alternate ways.

For example, referring to the embodiments shown in the Figures, the valve 18 can be a tubular, "O" ring type seal which is sized to compress against the bottom surface 52 of the valve retainer 32 and cover the outlet aperture 16. In this embodiment, the valve 18 is maintained against the bottom surface 52 by the elastic restoring force of the "O" ring which is stretched beyond its free diameter.

Figure 4:
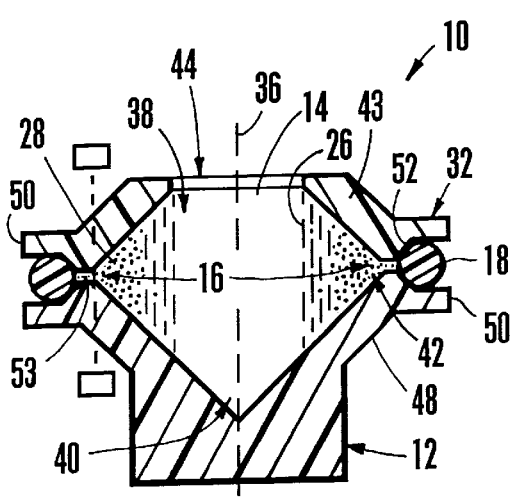
FIG. 4 is a cutaway view of the housing and the monitor of FIG. 3, with the housing being rotated at a separation speed.
Figure 5:
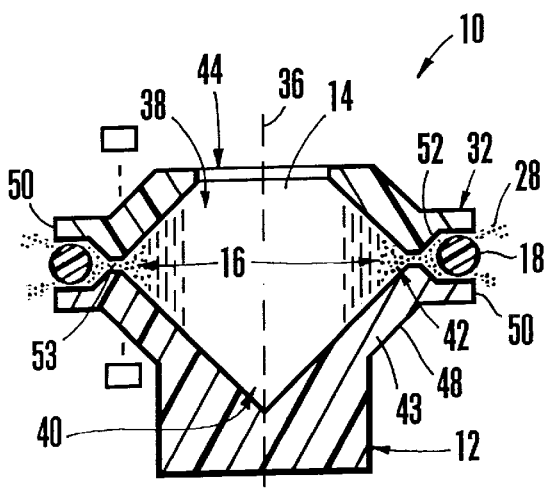
FIG. 5 is a cutaway view of the housing and the monitor of FIG. 4, with the housing being rotated at an expellant speed, the position of a valve is exaggerated for clarity.

During rotation of the housing 12, the "O" ring is subjected to centrifugal forces which tend to expand the "O" ring. As shown in FIGS. 3 and 4, the "O" ring is selected so that the "O" ring continues to seal the outlet aperture 16 while the housing 12 is spinning at or below the separation speed. However, as shown in FIG. 5, rotation of the housing 12 at or above the expellant speed causes the "O" ring to expand and unseal the outlet aperture 16. Stated another way, rotation at the expellant speed overcomes the elastic restoring force of the "O" ring type seal and causes the seal to expand radially. Thus, the unique design of the present separator 10 allows the operator to selectively open the valve 18 by selectively controlling the rotational speed of the housing 12. Importantly, the size and elasticity of the "O" ring can be varied to change the expellant speed.

Alternately, the valve 18 could be a discrete individual elastic element (not shown) which covers each outlet aperture 16 instead of the continuous "O" ring. However, this will be more difficult to assemble and manufacture.

It is anticipated that valve 18 can be designed to be self regulating. Stated another way, the valve 18 can be designed to that the valve 18 automatically closes after substantially all of the cells have been expelled, even though the housing 12 is being rotated at the expellant speed. A self regulating valve 18 is possible since the centrifugal force on the cells assists in the radial expansion of the "O" ring type seal. Thus, after the cells are expelled from the separation container 14, the amount of centrifugal force acting on the "O" ring type seal is reduced and the elastic restoring force will cause the valve 18 to close.

Referring to FIG. 1, the outer receptacle 20 substantially encircles the housing 12 and catches the first portion 28 which is expelled from the separation container 14. The outer receptacle 20 includes a hollow cylindrical wall 54 and a bottom 56 for catching the first portion 28. The outer receptacle 20 can also include a lid (not shown) and a drain 58 which is in fluid communication with a drain receptacle 60.

The spinner 22 spins the housing 12 to separate the first portion 28 from the second portion 30. The spinner 22 can be implemented in a number of alternate ways. For example, referring to FIG. 1, the spinner 22 can be a motor 62 which rotates an output shaft 64 that is attached to the housing 12. In this embodiment, the container axis 36 is generally coaxial with a central axis of the output shaft 64. Thus, rotation of the output shaft 64 causes rotation of the separation container 14 about the container axis 36. Axial rotation about the container axis 36 is preferred since the distance the cells must travel for separation from the serum or plasma is minimized. Importantly, axial centrifugation may occur when the separation container 14 is in a horizontal or other position. For example, the separation container 14 may be inverted.

Alternately, other devices which centrifuge or spin the separation container 14 may be used with the present invention.

The rate at which the spinner 22 rotates the housing 12 varies according to the design of the separator 10 and the type of sample 26. For a sample 26 of blood, the separator 10 initially rotates the housing 12 at a separation speed and subsequently rotates the housing 12 at a faster expellant speed. As shown in FIGS. 3 and 4, the valve 18 is not forced open during rotation of the housing 12 at or below the separation speed. However, during rotation at the separation speed, the heavier elements, e.g., the cells migrate or sediment in a shell which encircles the serum or plasma. Stated another way, rotation at the separation speed causes the sample 26 to separate into the first portion 28 and the second portion 30 within the separation container 14.

The separation speed varies according to the type of sample 26 and the desired time of separation. If a faster time of separation is desired, the separation speed is increased. Alternately, if a relatively long separation time is desired, a slower separation speed can be used. It is anticipated that a separation speed of between 1,000–4,000 RPM can be utilized with a sample 26 of blood. Typically, rotation of the separation container 14 at about 4,000 RPM, for about one (1) minute is sufficient to separate the cells from the plasma or serum in a sample 26 of blood.

After the first portion 28 is separated from the second portion 30 within the separation container 14, the rotation of the housing 12 is increased to the expellant speed. Referring to FIG. 5, the expellant speed is sufficient to open the valve 18. This allows the first portion 28, i.e., the cells, which are closest to the outlet aperture 16, to be centrifugally expelled from the separation container 14 through the outlet aperture 16. Rotation continues at the expellant speed until substantially all of the first portion 28 is exhausted from the separation container 14.

The desired expellant speed varies according to the type of sample 26 and desired time of expelling. If a faster time of expelling is desired, the expellant speed is increased. Alternately, if a long time of expelling is desired, a slower expellant speed can be used. It is anticipated that an expellant speed of between 5,000 and 9,000 RPM can be utilized with a sample 26 of blood.

Typically, the spinner 22 includes a controller 66 (see FIG. 1) which controls the rotational speed and rotational time of the housing 12. The controller 66 can control rotational speed of the spinner 22 by controlling voltage to the spinner 22.

The rotational time necessary to completely exhaust the cells can be determined empirically and depends upon the volume of sample 26 being separated and the expellant speed.

Alternately, the separator 10 can include a monitor 68 which monitors the separation container 14 and determines when substantially all of the first portion 28 is expelled from the separation container 14. The monitor 68 can be implemented in a number of alternate ways. For example, the monitor 68 can be positioned proximate the outlet aperture 16 and can determine when a change of transmittance occurs proximate the outlet aperture 16.

In the embodiment shown in FIG. 1, the monitor 68 includes an optics input 72 and an optics output 76. The optics input 72 directs a light beam 74 which passes through the separation container 14 and the sample 26 and is collected by the optics output 76. The light beam 74 is affected by the contents in its path. Since the cells are substantially more opaque to most wavelengths than the plasma or serum, the monitor 68 is able to determine when the light beam 74 passes through the plasma or serum by identifying a change of transmittance. After a change is detected, the separation container 14 contains only the second portion 30, namely the plasma or blood, and rotation of the separation container 14 is halted.

The optics input 72 can be a light-emitting diode (LED) providing the light beam 74. The optics output 76 can include a silicon photodiode monitor, a silicon phototransistor or a photometer which measures the amount of light received.

Alternately, for example, the monitor 68 can monitor the reflectance of the sample 26 proximate the outlet aperture 16.

Figure 8:
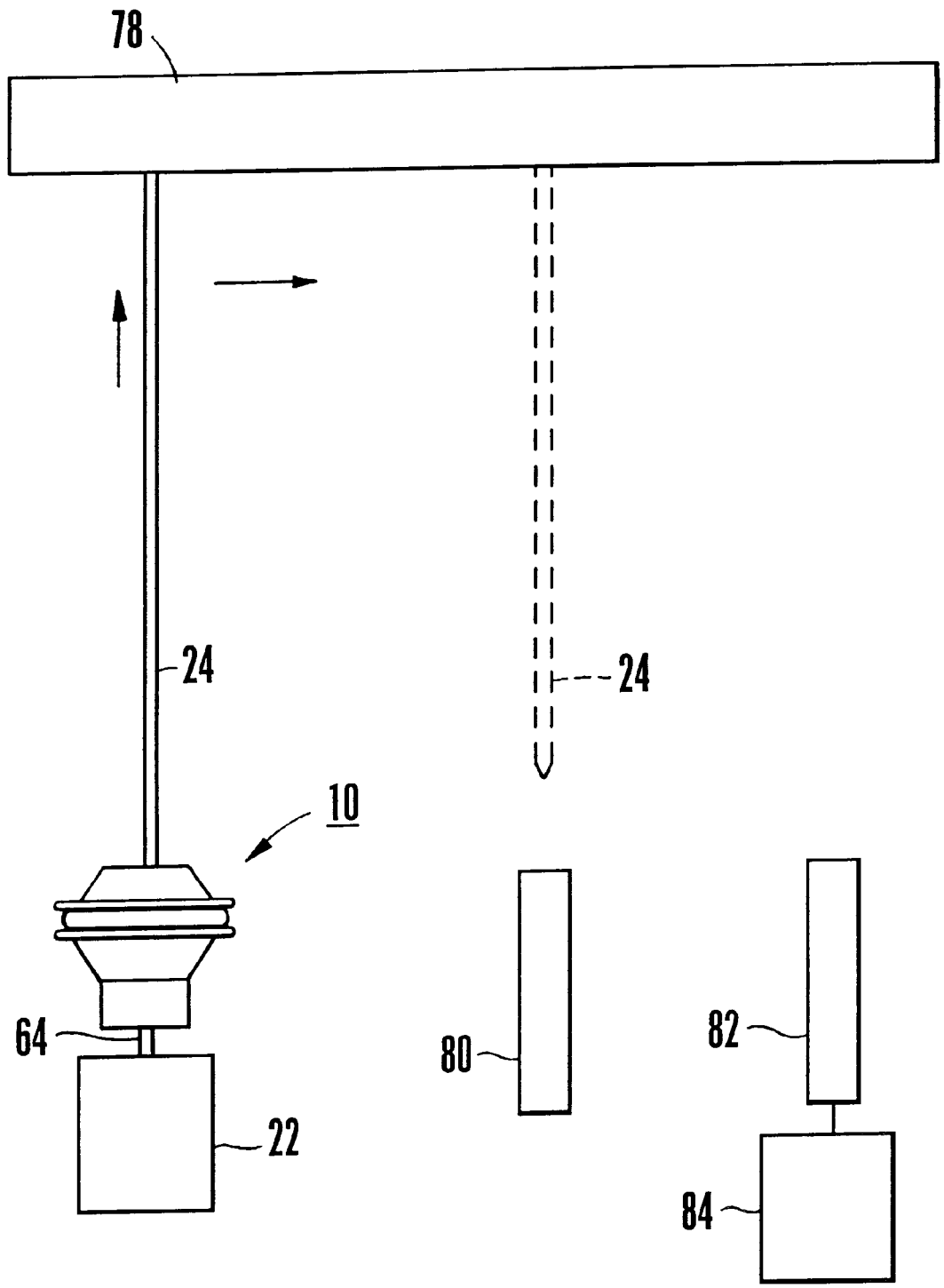
FIG. 8 is a simplified plan view of the separator of FIG. 1, configured for operation in accordance with the present invention.

Preferably, as shown in FIG. 8, the present invention includes a mover 78 which selectively allows the probe 24 to be moved relative to the separation container 14, a first receptacle 80 and a second receptacle 82. This allows the probe 24 to selectively transfer the sample 26, the first portion 28, and/or the second portion 30 between the separation container 14 and the first and second receptacles 80, 82.

The mover 78 can be implemented in a number of alternate ways. For example, the mover 78 can be a robotic arm which moves the probe 24 to the proper position in relation to the separation container 14, the first receptacle 80 or the second receptacle 82. Alternately, the mover 78 can be a device which moves the separation container 14 and the receptacles 80, 82 relative to the probe 24.

Depending upon the particular embodiment, the first receptacle 80 and second receptacle 82 can, for example, be either a cuvette or a flow cell for a clinical analyzer 84, a tube for a sample splitter, a waste receptacle, or a collection tube.

Referring again to FIG. 8, the separator 10 is incorporated as part of a clinical analyzer 84. A clinical analyzer 84 sold by Beckman Instruments, Inc. of Fullerton, Calif., the assignee of the present invention, under the trademark Synchron CX®3, can be utilized with the present invention. In this embodiment, the probe 24 can remove the sample 26 of whole blood from the first receptacle 80, i.e., a blood collection tube and transfer the sample 26 to the separator 10. Subsequently, after the sample 26 is separated by the separator 10, the serum or plasma can be collected with the probe 24 from the separation container 14 and transferred to the second receptacle 82, i.e., a cuvette of the clinical analyzer 84.

Alternately, the separator 10 can operate as a stand alone sample preparation station.

Importantly, the separator 10 quickly separates the sample 26 of blood without the use of a separating gel. This allows for the separation of the sample 26 at the laboratory, without batch processing of multiple samples 26. Further, if the separator 10 is an integral part of a clinical analyzer 84, the sample 26 of whole blood can be provided directly to the clinical analyzer 84, thereby eliminating any external preparation steps on the sample 26.

Moreover, since the sample 26 is not separated at a remote location by a batch processor, only an amount of test specimen needed for the test needs to be separated. The entire sample 26 does not have to be separated. This allows a single blood sample 26, in a single collection tube, to be used for both chemistry testing (need the liquid component of the sample 26) and hematology testing (separation makes the sample 26 unusable). This saves the cost of handling separate sample tubes and reduces the amount of sample 26 which must be removed from the patient.

OPERATION

Figure 2:
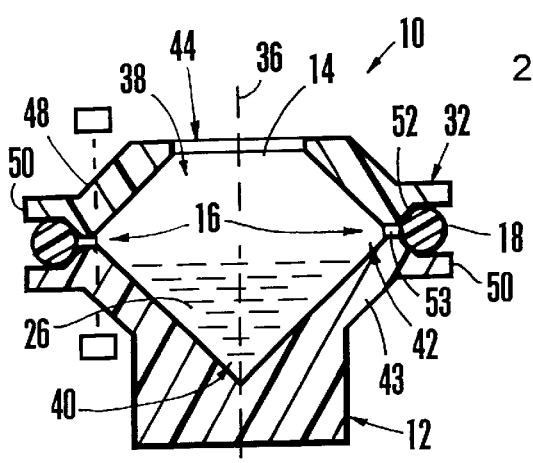
FIG. 2 is a cutaway view of a housing and a monitor from FIG. 1, taken on line 2—2 of FIG. 1, with a sample disposed in the housing.

The operation of the separator 10 can best be understood upon viewing FIGS. 2–7 in succession. FIG. 2 shows the sample 26 disposed in the separation container 14. FIG. 3 shows the separation container 14 after initial rotation about the container axis 36. Initial spinning of the housing 12 causes the sample 26 to move radially towards the outlet region 42 of the separation container 14.

FIG. 4 shows the separation container 14 rotated at the separation speed. Rotation at the separation speed, for a sufficient amount of time, causes the sample 26 to separate into generally concentric shells of the first portion 28 and the second portion 30 according to the relative densities. Since the cells have a higher density than the plasma or the serum, the sample 26 separates into an outer shell which is comprised of cells and an inner shell which is comprised of plasma or serum. Importantly, rotation at the separation speed is insufficient to cause the valve 18 to separate from the outlet aperture 16.

FIG. 5 shows the separation container 14 being rotated at the expellant speed. Rotation at this rate causes the valve 18 to separate from the separation container 14 and results in the first portion 28 exiting through the outlet aperture 16. Rotation of the separation container 14 at this rate is continued for a period of time sufficient to allow the majority of the first portion 28 to be centrifugally expelled through the outlet apertures 16. During this time, the monitor 68 can observe the composition of the sample 26 proximate the outlet apertures 16. When the monitor 68 determines that plasma or serum is proximate the outlet aperture 16, rotation of the separation container 14 is stopped and the valve 18 is allowed to seal the outlet aperture 16.

Figure 6:
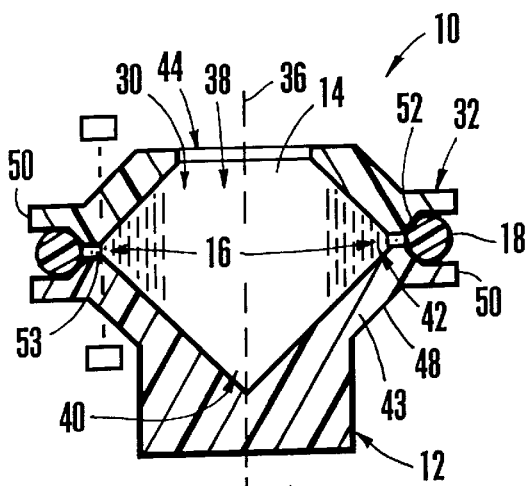
FIG. 6 is a cutaway view of the housing and the monitor of FIG. 5, after a first portion of the sample is expelled from the housing.

FIG. 6 shows the separation container 14 after complete exhaustion of the cells. Subsequently, rotation of the separation container 14 is stopped and the second portion 30 is allowed to settle proximate the proximal region 40 of the container 14.

Figure 7:
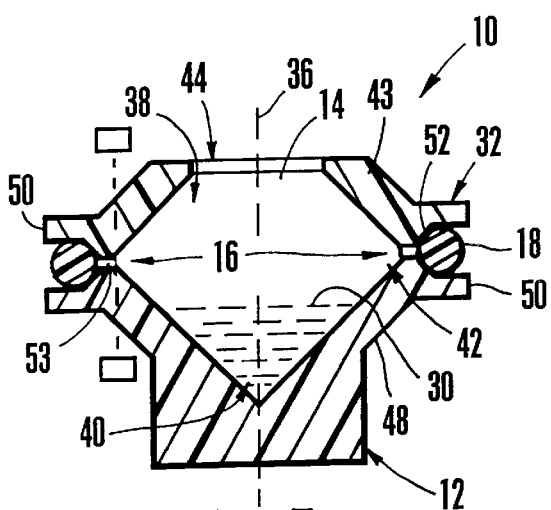
FIG. 7 is a cutaway view of the housing and the monitor of FIG. 6, after rotation of the housing is stopped, with a second portion of the sample remaining in the housing.

FIG. 7 shows the end result with only the second portion 30, i.e., the serum or plasma remaining in the separation container 14. The serum or plasma can readily be removed with the probe 24 and delivered to a cuvette of a clinical analyzer 84.

To reuse the separator 10, the residual sample 26 (not shown) is exhausted through the outlet apertures 16 by rotating the housing 12. Next, a wash fluid (not shown) is disposed into the separation container 14 and the housing 12 is rotated to remove traces of the sample 26 and prevent carryover between samples 26. Additional washes may be made as necessary. The duration and number of washes depends upon the acceptable levels of carryover. After the wash is complete, another sample 26 may be added and the process repeated.

While the particular separator 10 as herein shown and disclosed in detail is fully capable of obtaining the objects and providing the advantages herein before stated, it is to be understood that it is merely illustrative of embodiments of the present invention and that no limitations are intended to the details of construction or design herein shown other than as described in the appended claims. For example, it is anticipated that a separation gel, having a density higher than that of the serum or plasma, but lower than the cell can be used with the present invention. However, this would make the separator 10 more difficult to clean and would require an additional step to utilize.

What is claimed is:

1. A separator for separating a test specimen from cells in a sample of blood, the separator comprising:

a housing defining a separation container, the separation container having a container inlet;

an outlet aperture extending through the housing into the separation container, a motor means for selectively rotating the separation container at a separation speed and an expellant speed, wherein rotation of the separation container at the separation speed causes the cells to separate from the test specimen within the separation container; wherein the separation speed is at least one thousand RPM; wherein the expellant speed is faster than the separation speed; and a valve which substantially closes the outlet aperture during rotation of the separation container at the separation speed and opens during rotation of the separation container at the expellant speed.

2. The separator of claim 1 wherein the separation container includes a distal region, a proximal region, and an outlet region positioned between the distal region and the proximal region, and the separation container has a cross-section which is widest proximate outlet region.

3. The separator of claim 1 wherein the separation container includes an outlet region which is positioned proximate the outlet aperture and the separation container has a container diameter which is widest proximate the outlet region.

4. The separator of claim 3 compromising a retainer for retaining the valve; wherein the retainer includes a groove extending substantially circumferentially around an outer surface of the housing, proximate the outlet region and the valve includes a tubular seal disposed within the groove.

5. The separator of claim 4 wherein the outlet aperture includes a plurality of outlet holes extending through the housing between a bottom of the groove and the separation container.

6. A clinical analyzer including the separator of claim 1.

7. The separator of claim 1 including means for separating the test specimen from the cells in the sample of blood, the means for separating including (i) means for introducing the sample of blood into the separation container and (ii) means for spinning the housing with the motor to expel the cells through the outlet aperture.

8. The separator of claim 1 wherein the expellant speed is at least five thousand RPM.

9. The separator of claim 1 including a monitor which is adapted to detect the difference between the test specimen and cells.

10. The separator of claim 1 including a monitor which is adapted to detect when the test specimen is near the outlet aperture.

11. The separator of claim 1 including a monitor which is adapted to detect when substantially all of the cells have been expelled from the separation container.

12. A separator for separating a test specimen from cells in a sample of blood, the separator comprising:

a housing defining a separation container which is substantially symmetrical about a container axis, the separation container having a distal region, a proximal region, and an outlet region positioned between the distal region and the proximal region which substantially encircles the container axis, the separation container having a diameter which is widest proximate the outlet region and decreases towards the distal region and the proximal region, the separation container having a container inlet;

a valve retainer positioned proximate the outlet region, the valve retainer including a groove extending substantially circumferentially around an outer surface of the housing;

an outlet aperture extending through the housing between a bottom of the groove and the separation container;

a valve including a tubular seal disposed within the groove which substantially seals the outlet aperture during non-rotation of the housing;

a spinner for selectively rotating the separation container around the container axis at a separation speed which causes the cells to separate from the test specimen and an expellant speed which causes the valve to open and the cells to be expelled through the outlet aperture; and a monitor for directly monitoring the sample in the separation container.

13. A clinical analyzer including the separator of claim 12.

14. The separator of claim 12 wherein the spinner includes a controller which controls the rotational speed of the spinner; wherein the separation speed is less than the expellant speed; and wherein the separation speed is at least one thousand RPM, and the expellant speed is at least five thousand RPM.

15. The separator of claim 12 wherein the valve substantially closes the outlet aperture during rotation the separation container at the separation speed.

16. The separator of claim 12 wherein the monitor is adapted to detect the difference between the test specimen and cells.

17. A separator for separating a test specimen from cells in a sample of blood, the separator comprising:

a housing defining a separation container, the separation container having a container inlet;

an outlet aperture extending through the housing into the separation container;

a valve which substantially closes the outlet aperture during non-rotation of the housing and opens during rotation of the housing at an expellant speed; and a monitor for monitoring the sample proximate the outlet aperture to determine when substantially all of the cells have been expelled from the separation container.

18. The separator of claim 17 wherein the monitor is adapted to detect the difference between the test specimen and cells and the monitor is adapted to detect when the test specimen is proximate to the outlet aperture.

19. The separator of claim 17 wherein the monitor is adapted to detect when a change in transmittance occurs near the outlet aperture.

20. The separator of claim 17 wherein the monitor is adapted to detect when a change in reflectance occurs near the outlet aperture.

21. The separator of claim 17 comprising a spinner adapted to selectively rotate the separation container at a separation speed and the expellant speed, the rotation of the separation container at the separation speed causes the cells to separate from the test specimen within the separation container; wherein the valve substantially closes the outlet aperture during rotation of the separation container at the separation speed; and wherein the separation speed is less than the expellant speed.

22. A separator for separating a fluid sample into a first portion and a second portion, the first portion including cells and the second portion including a test specimen, the separator comprising:

a housing defining a separation container, the separation container having a container inlet;

an outlet aperture extending through the housing into the separation container;

a motor means for selectively rotating the separation container at a separation speed and an expellant speed, rotation of the separation container at the separation speed causes the first portion to separate from the second portion within the separation container; wherein rotation at the expellant speed is faster than rotation at the separation speed; and a valve which substantially closes the outlet aperture during rotation of the separation container at the separation speed and opens during rotation of the separation container at the expellant speed; wherein rotation of the separation container at the expellant speed causes the valve to open.

23. The separator of claim 22 wherein the separation speed is at least 1000 RPM.

24. A separator for separating a test specimen from cells in a sample of blood, the separator comprising:

a housing defining a separation container which is substantially symmetrical about a container axis, the separation container having a distal region, a proximal region, and an outlet region positioned between the distal region and the proximal region which substantially encircles the container axis, the separation container having a diameter which is widest proximate the outlet region and decreases towards the distal region and the proximal region, the separation container having a container inlet;

a valve retainer positioned proximate the outlet region, the valve retainer including a groove extending substantially circumferentially around an outer surface of the housing;

an outlet aperture extending through the housing between a bottom of the groove and the separation container;

a valve including a tubular seal disposed within the groove which substantially seals the outlet aperture during non-rotation of the housing;

a spinner for selectively rotating the separation container around the container axis at a separation speed which causes the cells to separate from the test specimen and an expellant speed which causes the valve to open and the cells to be expelled through the outlet aperture; and a controller which controls the rotational speed of the spinner; wherein the separation speed is less than the expellant speed; and wherein the separation speed is at least one thousand RPM, and the expellant speed is at least five thousand RPM.

* * * * *